United States Patent
Saito et al.

(10) Patent No.: US 10,213,530 B2
(45) Date of Patent: Feb. 26, 2019

(54) POLYMER FILM AND ANTIADHESIVE MATERIAL USING THE SAME

(71) Applicants: Toray Industries, Inc., Tokyo (JP); Nanotheta Co, Ltd., Tokyo (JP)

(72) Inventors: Akihiro Saito, Otsu (JP); Toru Arakane, Tokyo (JP); Kazuhiro Tanahashi, Otsu (JP); Koji Okabayashi, Tokyo (JP); Shinji Takeoka, Tokyo (JP); Toshinori Fujie, Tokyo (JP); Shoichiro Suzuki, Tokyo (JP); Atsushi Murata, Tokyo (JP); Shinya Otsubo, Tokyo (JP)

(73) Assignees: Toray Industries, Inc. (JP); Nanotheta Co, Ltd. (JP)

( * ) Notice: Subject to any disclaimer, the term of this patent is extended or adjusted under 35 U.S.C. 154(b) by 0 days.

(21) Appl. No.: 15/534,188

(22) PCT Filed: Jun. 17, 2016

(86) PCT No.: PCT/JP2016/068073
§ 371 (c)(1),
(2) Date: Jun. 8, 2017

(87) PCT Pub. No.: WO2016/204266
PCT Pub. Date: Dec. 22, 2016

(65) Prior Publication Data
US 2017/0348465 A1 Dec. 7, 2017

(30) Foreign Application Priority Data

Jun. 19, 2015 (JP) .................................. 2015-123855

(51) Int. Cl.
*C08G 81/02* (2006.01)
*C08G 63/06* (2006.01)
*C08G 63/664* (2006.01)
*C08J 5/18* (2006.01)
*C08L 53/00* (2006.01)
*A61L 31/04* (2006.01)
*A61L 27/00* (2006.01)
*A61L 31/00* (2006.01)
*A61L 15/00* (2006.01)
*C08G 81/00* (2006.01)
*C08G 65/332* (2006.01)
*A61L 15/50* (2006.01)
*C08G 65/331* (2006.01)

(52) U.S. Cl.
CPC ............. *A61L 31/041* (2013.01); *A61L 15/00* (2013.01); *A61L 15/50* (2013.01); *A61L 27/00* (2013.01); *A61L 31/00* (2013.01); *C08G 65/332* (2013.01); *C08G 65/3311* (2013.01); *C08G 81/00* (2013.01); *C08G 81/02* (2013.01); *C08J 5/18* (2013.01); *C08L 53/005* (2013.01); *C08L 2203/02* (2013.01)

(58) Field of Classification Search
None
See application file for complete search history.

(56) References Cited

U.S. PATENT DOCUMENTS

| | | | | |
|---|---|---|---|---|
| 5,711,958 A * | 1/1998 | Cohn | .................... | A61K 31/765 128/898 |
| 2006/0069168 A1* | 3/2006 | Tabata | .................. | A61L 24/046 514/772.1 |
| 2006/0189911 A1* | 8/2006 | Fukuhira | ................. | A61L 31/06 602/43 |
| 2008/0081888 A1 | 4/2008 | Kubo et al. | | |
| 2009/0311337 A1* | 12/2009 | Tanahashi | ............ | A61K 9/0019 424/497 |
| 2010/0062258 A1 | 3/2010 | Takeoka et al. | | |

FOREIGN PATENT DOCUMENTS

| | | |
|---|---|---|
| JP | 2001-327520 A | 11/2001 |
| JP | 2004-313759 A | 11/2004 |
| JP | 2008-106269 A | 5/2008 |
| JP | 2008-222768 A | 9/2008 |
| JP | 2009-029967 A | 2/2009 |
| JP | 2012-187926 A | 10/2012 |
| JP | 2014-140978 A | 8/2014 |
| JP | 2014-171590 A | 9/2014 |

OTHER PUBLICATIONS

Yan et al., Surface Science Techniques, Chapter 1 Contact Angle and Wetting Properties, Springer Series in Surface Sciences 51, pp. 3-34 (Year: 2013).*
Li et al., J. Appl. Polym. Sci., 131, pp. 1-5. (Year: 2014).*
Yaling et al., Polymer Materials Science and Engineering, 29(11) pp. 67-70 and 75. (Year: 2013).*
Tzong-Der Way et al., "Preparation and characterization of branched polymers as postoperative anti-adhesion barriers," Applied Surface Science, vol. 256, No. 10, 2010, pp. 3330-3336.
Yaling Lin et al., "Synthesis and characterization of star-shaped poly(ethylene glycol)-block-poly(L-lactic acid) copolymers by melt polycondensation," Journal of Applied Polymer Science, vol. 124, No. 6, Jun. 15, 2012, pp. 4496-4501.
Office Action dated Aug. 17, 2018, of counterpart Chinese Application No. 201680004090.9.

* cited by examiner

*Primary Examiner* — Abigail Vanhorn
(74) *Attorney, Agent, or Firm* — DLA Piper LLP (US)

(57) ABSTRACT

A polymer film can be adjusted to movement or a fine uneven surface of a living body and has excellent ability to adhere to a biological tissue. The polymer film includes a block copolymer having a structure in which branched polyalkylene glycol and polyhydroxyalkanoic acid are bound to each other, wherein the polymer film has a film thickness of 10 to 1000 nm. The branched polyalkylene glycol has at least three terminal hydroxyl groups per molecule, the mass percentage of the branched polyalkylene glycol relative to the total mass of the block copolymer is 1% to 30%, and a value obtained by dividing the average molecular weight of polyhydroxyalkanoic acid in the block copolymer by X that is the number of terminal hydroxyl groups present per a single molecule of the branched polyalkylene glycol is 10000 to 30000.

11 Claims, 1 Drawing Sheet

POLYMER FILM AND ANTIADHESIVE MATERIAL USING THE SAME

TECHNICAL FIELD

This disclosure relates to a polymer film and an antiadhesive material using the same.

BACKGROUND

In the field of medical care, it is known that films are applied to biological tissues for closure of the site of a surgical wound, protection of the site of a burn wound or the like, hemostasis, fixation of a device such as an infusion line to the skin, prevention of adhesion of an organ and the like. Those films are required to have the ability to firmly attach to biological tissue and flexibility or strength that allows the films to follow movement of a living body to prevent bleeding from an opened wound, exposure of the biological tissue, detachment of a device fixed to the biological tissue, organ adhesion, and the like.

In addition, when such films are used in vivo, if a film is permanently left in vivo, it may lead to complications such as infection and inflammation, and it may also result in requiring re-operation to remove the film. It is therefore necessary for the film to be biodegradable so that it is degraded and disappears in vivo after fulfilling its role.

Known biodegradable films include films comprising biodegradable polymers such as polylactic acid, polylactone, and copolymers containing blocks of such polymers. For example, JP Patent Publication (Kokai) Nos. 2014-140978 A and 2012-187926 A each disclose a film comprising a biodegradable polymer and having a nanometer film thickness that can adhere to biological tissue. In addition, JP Patent Publication (Kokai) Nos. 2001-327520 A and 2004-313759 A each disclose a biodegradable film having hydrophilicity and biological affinity that contains a block copolymer.

The films disclosed in JP '978 and JP '926 are, however, highly hydrophobic and therefore they are considered to have a low affinity to the surface of a living body in a humid environment. Further, as a crystalline copolymer having a high glass-transition temperature is used, even when a thin film is made, the film is hardly deformed. Such film cannot sufficiently follow movement of a living body or cannot be adjusted to biological tissue having a fine uneven surface, which has been problematic. In addition, as the films disclosed in JP '520 and JP '759 have high adhesiveness to biological tissues, they have not been examined in terms of film thickness. It is unclear whether they have sufficient properties required when used as an antiadhesive material.

It could therefore be helpful to provide a polymer film that can be adjusted to movement or a fine uneven surface of a living body and has excellent ability to adhere to biological tissue.

SUMMARY

We found that a polymer film having excellent ability to adhere to biological tissue can be produced using, as a material, a block copolymer comprising a branched polyalkylene glycol block and a polyhydroxyalkanoic acid block.

We thus provide:

(1) A polymer film, comprising a block copolymer having a structure in which branched polyalkylene glycol and polyhydroxyalkanoic acid are bound to each other, wherein the branched polyalkylene glycol has at least three terminal hydroxyl groups per molecule, the mass percentage of the branched polyalkylene glycol relative to the total mass of the block copolymer is 1% to 30%, a value obtained by dividing the average molecular weight of polyhydroxyalkanoic acid in the block copolymer by X that is the number of terminal hydroxyl groups present per a single molecule of the branched polyalkylene glycol is 10000 to 30000, and the polymer film has a film thickness of 10 to 1000 nm.

(2) The polymer film according to (1), wherein the branched polyalkylene glycol has a structure in which linear polyethylene glycol is bound to polyalcohol.

(3) The polymer film according to (1) or (2), wherein the branched polyalkylene glycol has 3 to 8 terminal hydroxyl groups.

(4) The polymer film according to any one of (1) to (3), wherein the branched polyalkylene glycol has an average molecular weight of 5000 to 30000.

(5) The polymer film according to any one of (1) to (4), wherein the block copolymer has an average molecular weight of 40000 to 200000.

(6) The polymer film according to any one of (1) to (5), wherein the block copolymer is represented by formula (I):

(where m denotes an integer of 0 to 4, each of n, o, p, q, and r independently denotes an integer of 36 to 126, each of v, w, x, y, and z independently denotes an integer of 91 to 376) or formula (II):

(where s denotes an integer of 81 to 126, and t denotes an integer of 220 to 377).

(7) The polymer film according to any one of (1) to (6), wherein the Young's modulus is from 20 MPa to 700 MPa.

(8) The polymer film according to any one of (1) to (7), wherein the receding contact angle is less than 60°.

(9) A laminated film, wherein a water-soluble film comprising a water-soluble polymer is laminated on at least one side of the polymer film according to any one of (1) to (8).

(10) An antiadhesive material, which comprises the polymer film according to any one of (1) to (8) or the laminated film according to (9).

(11) A polymer film, comprising a block copolymer having a structure in which branched polyalkylene glycol and polyhydroxyalkanoic acid are bound to each other, wherein
the polymer film has a film thickness of 10 to 1000 nm,
the branched polyalkylene glycol has at least three terminal hydroxyl groups per molecule,
the mass percentage of the branched polyalkylene glycol relative to the total mass of the block copolymer is 1% to 30%, and
a value obtained by dividing the average molecular weight of polyhydroxyalkanoic acid in the block copolymer by X that is the number of terminal hydroxyl groups present per a single molecule of the branched polyalkylene glycol is 10000 to 30000.

(12) The polymer film according to (11), wherein the branched polyalkylene glycol has a structure in which linear polyethylene glycol is bound to polyalcohol.

(13) The polymer film according to (11) or (12), wherein the branched polyalkylene glycol has 3 to 8 terminal hydroxyl groups.

(14) The polymer film according to any one of (11) to (13), wherein the branched polyalkylene glycol has an average molecular weight of 5000 to 30000.

(15) The polymer film according to any one of (11) to (14), wherein the block copolymer has an average molecular weight of 40000 to 200000.

(16) The polymer film according to any one of (11) to (15), wherein the block copolymer is represented by formula (I):

(where m denotes an integer of 0 to 4, each of n, o, p, q, and r independently denotes an integer of 36 to 126, each of v, w, x, y, and z independently denotes an integer of 91 to 376) or formula (II):

(where s denotes an integer of 81 to 126, and t denotes an integer of 220 to 377).

(17) The polymer film according to any one of (11) to (16), wherein the Young's modulus is from 20 MPa to 700 MPa.

(18) The polymer film according to any one of (11) to (17), wherein the receding contact angle is less than 60°.

(19) A laminated film, wherein a water-soluble film comprising a water-soluble polymer is laminated on at least one side of the polymer film according to any one of (11) to (18).

(20) An antiadhesive material, which comprises the polymer film according to any one of (11) to (18) or the laminated film according to (19).

The polymer film has excellent ability to adhere to biological tissue and follow movement or a fine uneven surface of a living body and, therefore, is useful as an antiadhesive material, a wound closure material, a hemostatic material, a material for fixing a medical device or the like.

This description includes part or all of the content as disclosed in the description and/or drawings of JP No. 2015-123855.

DETAILED DESCRIPTION

Figure 1:
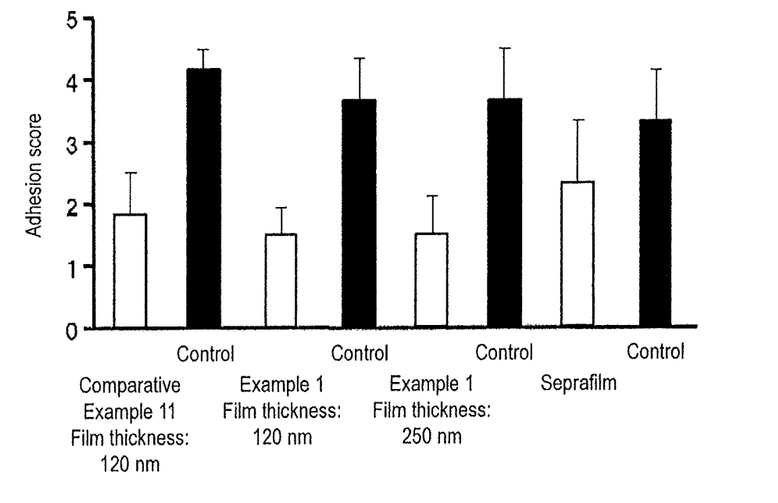
The FIGURE is a graph showing the results of evaluation of ability to prevent adhesion using the serosal dissection model mice in the Examples.

The polymer film contains a block copolymer having a structure in which branched polyalkylene glycol and polyhydroxyalkanoic acid are bound to each other. Preferably, polyhydroxyalkanoic acid is bound to the terminus of a polyalkylene glycol chain of branched polyalkylene glycol. Branched polyalkylene glycol has at least three terminal hydroxyl groups per molecule. The polymer film contains the above block copolymer at preferably 90% by mass or more and particularly preferably 95% by mass or more relative to its total mass (or the mass of a polymer film alone when a water-soluble thin-film layer is laminated on a polymer film as described below).

The term "film" refers to a two-dimensionally extended construct, the concept of which encompasses a sheet, a plate, a non-continuous film and the like. The film may have fine pores or it may be a porous film.

In addition, the material having "biocompatibility" or "biological affinity" is a material that causes no or substantially no stimulation or negative influence on a biological tissue. More specifically, it is meant that such material does not cause generation or elution of a substance harmful to a biological tissue, and a biological tissue does not show a protective response such as inflammation or blood coagulation by recognizing the material as a foreign body when coming into contact with it. Preferably, the polymer film has biocompatibility.

Branched Polyalkylene Glycol

Branched polyalkylene glycol has a number X of terminal hydroxyl groups. X is preferably 3 or more and more preferably 4 or more. The structure of branched polyalkylene glycol is not particularly limited. However, branched polyalkylene preferably has a structure in which polyalkylene glycol, or specifically, linear polyalkylene glycol is bound to at least some of hydroxyl groups of polyalcohol. Polyalcohol has preferably at least 3 hydroxyl groups and more preferably at least 4 hydroxyl groups. Specific examples of polyalcohol include: glycerin, polyglycerin (or specifically dimeric to hexameric glycerine), and pentaerythritol; and sugars such as glucose, fructose, xylose, galactose, mannose, erythrose, arabinose, sucrose, maltose, lactose, trehalose and cellobiose. These examples of polyalcohol are particularly preferable because of their biocompatibility.

Preferably, polyalkylene glycol is bound to all hydroxyl groups of polyalcohol. However, this disclosure is not limited thereto. Polyalkylene glycol is not necessarily bound to some of hydroxyl groups of polyalcohol. When the number of polyalkylene glycol chains is excessively small, intermolecular interaction decreases while, on the other hand, when it is excessively large, steric hindrance occurs, which might result in reduction of copolymerization reactivity, film formation performance and mechanical properties. In view of the above, the number of polyalkylene glycol chains bound to a single polyalcohol molecule is preferably 3 to 8. In more detail, it is preferable that linear polyalkylene glycol is bound to 3 to 8 hydroxyl groups of polyalcohol so that branched polyalkylene glycol, in which 3 to 8 hydroxyl groups are present at the terminus of polyalkylene glycol, is constructed.

When the molecular weight of branched polyalkylene glycol is excessively large, branched polyalkylene glycol is unlikely to be metabolized in vivo. Meanwhile, when it is excessively small, hydrophilicity of a polymer film decreases, which might cause not only reduction of biocompatibility but also negative influence on physical properties of the polymer film. In view of this, the average molecular weight of branched polyalkylene glycol is preferably 5000 to 30000.

When the content of branched polyalkylene glycol is excessively low, flexibility of a film becomes insufficient, which makes the film unable to follow a biological tissue. On the other hand, when it is excessively high, film formation performance during film formation decreases while water solubility excessively increases, causing a film to be dissolved immediately after being attached to a living body. In view of this, the mass percentage of branched polyalkylene glycol block relative to the total mass of a block copolymer is preferably 1% or more and particularly preferably 5% or more while it is preferably 30% or less and particularly preferably 25% or less. It is within a range of specifically 1% to 30% and more specifically 5% to 30%.

In addition, for branched polyalkylene glycol and polyhydroxyalkanoic acid described in detail below, the mass percentage relative to the total mass of a block copolymer and the average molecular weight can be calculated based on the integral of chemical shift signals of protons, the number of hydrogen atoms in a repeating unit, and the molecular weight of a repeating unit obtained by $^1$H-NMR measurement of a block copolymer, which are derived from a chemical structure specific to either polyalkylene glycol or polyhydroxyalkanoic acid.

For example, in a block copolymer comprising branched polyalkylene glycol and a poly(lactic acid-glycolic acid) copolymer, given that A denotes a relative integral of signals of a chemical shift from 3.4 to 3.7 ppm derived from 4 hydrogen atoms of an ethylene group of polyethylene glycol, B denotes a relative integral of signals of a chemical shift from 1.4 to 1.6 ppm derived from 3 hydrogen atoms of a methyl group of a lactic acid unit, and C denotes a relative integral of signals of a chemical shift from 4.7 to 4.9 ppm derived from 2 hydrogen atoms of a methylene group of a glycolic acid unit, the mass proportions of branched polyalkylene glycol and polyhydroxyalkanoic acid relative to the total mass of the block copolymer are represented by Formulae (1) and (2), respectively, with the use of molecular weights of 44, 72, and 58 for the corresponding repeating units. In addition, each of the average molecular weights of branched polyalkylene glycol and polyhydroxyalkanoic acid can be calculated by multiplying the average molecular weight of the block copolymer by the corresponding mass proportion.

Mass proportion of branched polyalkylene glycol (%)=
100×(44×A/4)/((44×A/4)+(72×B/3)+(58×C/2))    (1)

Mass proportion of polyhydroxyalkanoic acid (%)=
100×((72×B/3)+(58×C/2))/((44×A/4)+(72×B/3)+(58×C/2))    (2)

Specifically, branched polyalkylene glycol can be polyalcohol, to which polyethylene glycol or polypropylene glycol is bound. Examples of such branched polyalkylene glycol that can be preferably used include the "SUNBRIGHT (registered trademark) PTE" series (having a structure in which a polyethylene glycol chain is bound to hydroxyl groups of pentaerythritol) and the "SUNBRIGHT (registered trademark) HGEO" series (having a structure in which polyethylene glycol is bound to hydroxyl groups of polyglycerin having 8 hydroxyl groups), which are commercially available from NOF Corporation.

Polyhydroxyalkanoic Acid

Polyhydroxyalkanoic acid may be a polymer of biodegradable hydroxyalkanoic acid. It may be a homopolymer comprising one type of hydroxyalkanoic acid monomer or a copolymer of two or more types of hydroxyalkanoic acid monomers. Examples of a hydroxyalkanoic acid monomer include lactic acid, 3-hydroxybutanoic acid, glycolic acid and ε-caprolactone. A hydroxyalkanoic acid monomer may be an L- or D-form monomer. In some cases, the polymer may be a mixture of a D-form monomer and an L-form monomer (DL-form). In consideration of excellent physical properties such as mechanical strength, a homopolymer consisting of a D- or L-form monomer is preferable. Specifically, poly L-lactic acid or poly D-lactic acid consisting of L-lactic acid or D-lactic acid is most preferable.

When the molecular weight of polyhydroxyalkanoic acid in a block copolymer is excessively large, it causes reduction of hydrophilicity, resulting in reduction of biocompatibility. Meanwhile, when it is excessively small, it causes reduction of intermolecular interaction, resulting in reduction of film formation performance, thereby making it impossible to obtain a film having sufficient strength. In view of this, the average molecular weight of polyhydroxyalkanoic acid per branched chain, which is a value obtained by dividing the average molecular weight of polyhydroxyalkanoic acid in a block copolymer by the number (X) of terminal hydroxyl groups of a single molecule of branched polyalkylene glycol, is preferably 10000 to 30000.

Block Copolymer

When a block copolymer in the polymer film has an excessively large average molecular weight, viscosity thereof increases during melting at a high temperature, making it difficult to produce a film. Meanwhile, when it has an excessively small average molecular weight, it causes reduction of intermolecular interaction, resulting in reduction of film formation performance, thereby making it impossible to obtain a film having sufficient strength. In view of this, the average molecular weight of a block copolymer, which is determined by gel permeation chromatography (GPC), is preferably 40000 or more, more preferably 200000 or less, and particularly preferably 150000 or less. It is within a range of specifically 40000 to 200000 and more specifically 40000 to 150000.

One specific example of such block copolymer is a block copolymer having a structure represented by general formula (I) or (II):

In general formula (I), m denotes an integer of 0 to 4, each of n, o, p, q, and r independently denotes an integer of 36 to 126, and each of v, w, x, y, and z independently denotes an integer of 91 to 376.

In general formula (II), s denotes an integer of 81 to 126, and t denotes an integer of 220 to 377.

Branched polyalkylene glycol and polyhydroxyalkanoic acid can be bound by an arbitrary method upon production of the block copolymer. Examples of the method include a method in which hydroxyalkanoic acid is polymerized starting from the terminal hydroxyl group of a polyalkylene glycol chain and a method in which branched polyalkylene glycol and polyhydroxyalkanoic acid are bound via a condensation reaction. In particular, the block copolymer is most preferably a block copolymer having a structure in which linear polyhydroxyalkanoic acid is bound to the terminus of the linear polyalkylene glycol chain of branched polyalkylene glycol because such block copolymer has strong mechanical strength.

The block copolymer can be obtained by, for example, conducting ring-opening polymerization of a cyclic ester intermediate of hydroxyalkanoic acid such as lactide under reduced pressure using a catalyst such as tin octylate in the presence of branched polyalkylene glycol defined herein. Known methods for production of polyhydroxyalkanoic acid can be used as a method of removing moisture or a low-molecular-weight compound by adjusting conditions for heat reflux in an organic solvent for conducting a polymerization reaction or a method of deactivating a catalyst after the end of a polymerization reaction to inhibit a depolymerization reaction. For example, the obtained block copolymer is heat treated under reduced pressure, thereby making it possible to remove an unreacted cyclic ester intermediate via sublimation.

Polymer Film

The polymer film may contain various additives as well as the block copolymer unless physical properties of the polymer film are impaired. The amount of additives accounts for preferably 0% to 5% by mass of the total mass of a polymer film. Examples of additives include antioxidants, weathering stabilizers, heat stabilizers, lubricants, crystal nucleating agents, ultraviolet absorbers and colorants. The polymer film may contain different types of additives.

In addition, the polymer film may contain particles of an inorganic or organic compound in addition to the above additives unless physical properties of the polymer film are impaired. The amount of the particles accounts for preferably 0% to 5% by mass of the total mass of a polymer film. Examples of such particles include: particles comprising calcium carbonate, titanium dioxide, silicon dioxide, calcium fluoride, lithium fluoride, alumina, barium sulfate, zirconia, and calcium phosphate; cross-linked polystyrene particles; and metallic nanoparticles.

In view of flexibility, mechanical strength, and ability to follow the shape of an object of attachment, the film thickness of the polymer film is preferably 10 nm or more and particularly preferably 50 nm or more while it is preferably 1000 nm or less and particularly preferably 500 nm or less. It is within a range of specifically 10 to 1000 nm and more specifically 10 to 500 nm. In the above range, the film shape can be easily maintained and wrinkles are unlikely to be formed upon attachment of the film, which are preferable.

When elasticity of the polymer film is excessively high, the film becomes less bendable, resulting in decreased ability to follow an object of attachment and decreased adherability. In view of this, the Young's modulus of the polymer film is preferably 700 MPa or less and particularly preferably 100 MPa or less. In addition, when elasticity of the film is excessively low, the film becomes less resilient, making it difficult to handle the film. In view of this, the Young's modulus of the polymer film is preferably 20 MPa or more and particularly preferably 30 MPa or more. Specifically, the Young's modulus is preferably 20 to 700 MPa and particularly preferably 30 to 100 MPa. The term "Young's modulus" refers to a value determined by the Strain-Induced Elastic Buckling Instability for Mechanical Measurements (SIEBIMM) technique described below.

Regarding the ability to adhere to a biological tissue that is an object of attachment, a value determined by the attachment test using a commercially available skin model described below can be used as an index for the polymer film. When adherence strength (detachment strength) is excessively high, a tissue is pressed and inflammation is induced, while on the other hand, when it is excessively low, the film is detached from the object of attachment, which results in disposition of the film and may cause bleeding or adhesion. In view of this, it is preferable that adherence strength of the polymer film is preferably 0.15 N/cm or more and particularly preferably 0.2 N/cm or more while it is preferably 0.75 N/cm or less and particularly preferably 0.35 N/cm or less. It is within a range of specifically 0.15 to 0.75 N/cm and more specifically 0.2 to 0.35 N/cm. A polymer film having preferably adherence force is highly hydrophilic and has, for example, a receding water contact angle of preferably less than 60°, more preferably 50°, and particularly preferably less than 40°.

A water-soluble thin-film layer may be laminated on at least one side of the polymer film to improve handleability. Examples of a material for a water-soluble thin-film layer include water-soluble polymers such as polyvinyl alcohol, polyvinylpyrrolidone, polyethylene glycol, polypropylene glycol, alginic acid, hyaluronic acid, acetylhyaluronic acid, pullulan, chitin and chitosan. A water-soluble thin-film layer may be in any form such as film, sheet, woven fabric, knit or non-woven fabric. A polymer film on which such water-soluble thin-film layer is laminated is useful particularly for medical applications such as a wound wrapper material, an antiadhesive material, a hemostatic material, a sealant material, a plaster, a material for fixing lines/tubes and an adhesive carrier for absorption of drugs through tissue.

The polymer film can be produced by a known technique such as spin coating, gravure coating, lip direct coating, slot coating, comma coating, inkjet or silk screen printing. Examples of a base material for supporting a polymer film in production steps that can be used include a glass base material, a metal base material and a plastic base material. In view of economy and surface smoothness, a plastic base material such as a plastic film is preferable. Before coating of a starting material polymer, it is more preferable to conduct treatment to promote adhesiveness such as corona discharge treatment in the air, nitrogen gas, a mixed gas of nitrogen/carbon dioxide, or a different atmosphere, plasma treatment under reduced pressure, flame treatment or ultraviolet treatment. Further, a base material may be subjected to anchor treatment using an anchor treatment agent such as urethane resin, epoxy resin or polyethylenimine.

When a biaxially oriented film comprising polyester such as polyethylene terephthalate or polyolefin such as polypropylene is used as a plastic base material, it is possible to produce the polymer film by either off-line coating comprising coating a starting material polymer after a step of biaxially oriented film formation or in-line coating comprising coating a starting material polymer in a step of biaxially oriented film formation.

In production by in-line coating, it is preferable to conduct coating before heat fixation of the polymer film. It is therefore preferable to conduct coating of an unoriented film, a film obtained immediately after monoaxial orientation in the longitudinal or transverse direction, or film obtained immediately after biaxial orientation. The term "heat fixation" refers to a step of crystallizing a film via heat treatment during which an oriented film is maintained at a temperature above the orientation temperature and below the melting temperature of the film.

In production by off-line coating, a solution obtained by dispersing a starting material polymer in a solvent is applied by a technique such as gravure coating, reverse coating, spray coating, kiss coating, comma coating, die coating, knife coating, air knife coating or metaling bar coating for film formation. It is possible to form a film at a relatively high speed via off-line coating.

The coating film of a starting material polymer can be dried by a heat roll contact method, a heating medium (e.g., air or oil) contact method, an infrared heating method, a microwave heating method or the like. The drying temperature is preferably 80° C. to 180° C. for in-line coating and 60° C. to 110° C. for off-line coating. The drying time is preferably 1 to 60 seconds and more preferably 3 to 30 seconds.

The polymer film and a laminated film obtained using the same have flexibility that allows them to be attached to various surfaces such as flat surfaces, high-curvature surfaces, and uneven surfaces. Thus, it is possible to attach such films to any type of in vivo or in vitro tissue in an environment in which moisture exists. Therefore, the films are particularly useful as an antiadhesive material for preventing adhesion derived from wounds on the skin or organ opened in surgery and also as a material for closing such wounds or a hemostatic material. In addition, they can be used as a fixation material for fixing lines and tubes to the patient's skin or an attachment carrier for transdermal or transmucosal administration of drugs. Further, they also can be used for non-medical skin care applications.

EXAMPLES

1. Preparation of a Starting Material Polymer

Example 1

L-lactide (75 g; PURAC biochem BV) and dehydrated SUNBRIGHT (registered trademark) PTE-10T (25 g; a four-branched polyalkylene glycol derivative (pentaerythritol polyethylene glycol); NOF Corporation) were mixed in a flask under the nitrogen airflow, heated at 140° C. to be melted, and further mixed. Then, the mixture was heated to 180° C., and tin dioctoate (8.1 mg; Wako Pure Chemical Industries, Ltd.) added to react with the mixture. Thus, a block copolymer was obtained. The obtained polymer was dissolved in chloroform, washed with dilute hydrochloric acid, and added dropwise to an excessive amount of methanol. A polylactic acid-polyethylene glycol block copolymer having an average molecular weight of 85000 was obtained as a precipitate by the GPC method. The mass percentage of the polyethylene glycol block relative to the total mass was 25%. The average molecular weight of the polylactic acid block was divided by 4, which was the number of branched chains. The obtained value was 15938. Dichloromethane was used as a solvent for film formation.

Example 2

A polylactic acid-polyethylene glycol block copolymer having an average molecular weight of 131000 was obtained by the GPC method in the same manner described in Example 1 except that 85 g of DL-lactide and 17 g of dehydrated SUNBRIGHT (registered trademark) PTE-10T were mixed. The mass percentage of the polyethylene glycol block relative to the total mass was 17%. The average molecular weight of the polylactic acid block was divided by 4, which was the number of branched chains. The obtained value was 27183. Dichloromethane was used as a solvent for film formation.

Example 3

A polylactic acid-polyethylene glycol block copolymer having an average molecular weight of 111000 was obtained by the GPC method in the same manner described in Example 1 except that 85 g of DL-lactide and 15 g of dehydrated SUNBRIGHT (registered trademark) HGEO-50H (eight-branched polyalkylene glycol derivative; NOF Corporation) were mixed. The mass percentage of the polyethylene glycol block relative to the total mass was 13%. The average molecular weight of the polylactic acid block was divided by 8, which was the number of branched chains. The obtained value was 12071. Dichloromethane was used as a solvent for film formation.

Comparative Example 1

Poly DL-lactic acid (PURAC; PURASORB (registered trademark) PDL20; weight average molecular weight in terms of reference polymethyl methacrylate (PMMA): 565000) was used as a starting material polymer. The mass percentage of a polyethylene glycol block relative to the total mass was 0%. Ethyl acetate was used as a solvent for film formation.

Comparative Example 2

A polylactic acid-polyethylene glycol block copolymer having an average molecular weight of 88400 was obtained by the GPC method in the same manner described in Example 1 except that 75 g of DL-lactide and 17 g of dehydrated SUNBRIGHT (registered trademark) HGEO-10T (eight-branched polyalkylene glycol derivative; NOF Corporation) were mixed. The mass percentage of the polyethylene glycol block relative to the total mass was 25%. The average molecular weight of the polylactic acid block was divided by 8, which was the number of branched chains. The obtained value was 8288. Dichloromethane was used as a solvent for film formation.

Comparative Example 3

A polylactic acid-polyethylene glycol block copolymer having an average molecular weight of 83000 was obtained by the GPC method in the same manner described in Example 1 except that 50 g of L-lactide and 50 g of dehydrated SUNBRIGHT (registered trademark) MEH-20T (unbranched polyethylene glycol derivative (methoxypolyethylene glycol); NOF Corporation) were mixed. The mass percentage of the polyethylene glycol block relative to the total mass was 50%. The average molecular weight of the polylactic acid block was divided by 1, which was the number of branched chains. The obtained value was 41500. Dichloromethane was used as a solvent for film formation.

Comparative Example 4

A poly(lactic acid/glycolic acid)-polyethylene glycol block copolymer having an average molecular weight of 84500 was obtained by the GPC method in the same manner described in Example 1 except that 45 g of L-lactide, 50 g of dehydrated SUNBRIGHT (registered trademark) MEH-20T (unbranched polyethylene glycol derivative (methoxypolyethylene glycol); NOF Corporation), and 15 g of glycolide (PURAC biochem BV) were mixed. The mass percentage of the polyethylene glycol block relative to the total mass was 50%. The average molecular weight of the polylactic acid block was divided by 1, which was the number of branched chains. The obtained value was 42250. Dichloromethane was used as a solvent for film formation.

Comparative Example 5

A poly(lactic acid/glycolic acid)-polyethylene glycol-poly(lactic acid/glycolic acid) block copolymer having an average molecular weight of 187200 was obtained by the GPC method in the same manner described in Example 1 except that 45 g of L-lactide, SUNBRIGHT (registered trademark) DKH-20T (polyethylene glycol; NOF Corporation), and 20 g of glycolide were mixed. The mass percentage of the polyethylene glycol block relative to the total mass was 33%. The average molecular weight of the poly (lactic acid/glycolic acid) block was divided by 2, which was the number of branched chains. The obtained value was 62712. Dichloromethane was used as a solvent for film formation.

2. Film Formation Method (1) Spin Coating Method
(i) Base Material
P-type silicon wafer (diameter: 100±0.5 mm; thickness: 525±25 μm; oxide film: 200 nm; crystal plane index: 100; KST World Corp.) was cut to a size of 40 mm×40 mm and used. The silicon substrate was immersed in a solution containing sulfuric acid and hydrogen peroxide water at a volume ratio of 3:1 for 10 minutes before use and then washed with deionized water (resistivity: 18 Ωcm).

(ii) Film Formation

At first, a 2% by weight polyvinyl alcohol (PVA) aqueous solution was applied to the silicon substrate, followed by spin coating (4000 rpm; 20 seconds; Opticoat (registered trademark) MS-A150; Mikasa Co., Ltd.). Thus, a water-soluble film was formed. Next, solutions obtained by dissolving the polymers described in the Examples and the Comparative Examples were each separately applied thereto and spin coating (4000 rpm; 20 seconds) performed to form a polymer film having a desired thickness. Thus, laminated films each having a water-soluble film and a polymer film laminated on the silicon substrate were obtained.

The laminated films were each separately immersed in water, together with the silicon substrate, thereby dissolving the water-soluble film to cause the polymer film to be detached. Self-support ability of each polymer film was evaluated. The polymer film detached in water was scooped with a wire loop and attached via ethanol to a pullulan film (film thickness: about 10 μm) prepared on a polystyrene dish by the casting method, followed by drying. The obtained polymer films, each of which was supported by the pullulan film, were used for evaluation of ability to prevent adhesion.

(2) Gravure Coating Method

A 2% by weight PVA aqueous solution was applied to a polyethylene terephthalate (PET) film (Lumirror (registered trademark) type T60; Toray Industries, Inc.; thickness: 25 μm) having a width of 12 cm using a microgravure printer (Yasui Seiki Inc.; Mini-Labo machine) so that a water-soluble film was formed. Solutions obtained by dissolving the polymers described in the Examples and the Comparative Examples were each separately applied thereto to form a polymer film having a desired thickness. Thus, laminated films each having a water-soluble film and a polymer film laminated on the PET film were obtained. The Mini-Labo machine was operated under the following conditions: gravure roll rotation speed: 30 rpm; line speed: 1.3 m/minute; drying temperature: 80° C. for an ethyl acetate solvent or room temperature for a dichloromethane solvent. The laminated film were each separately immersed in water, thereby dissolving the water-soluble film to cause the polymer film to be detached from the PET film. The Young's modulus, contact angle, and degree of attachment were determined for the obtained polymer films.

3. Evaluation of Film Properties (1) Average Molecular Weight of Block Copolymer The average molecular weight of a block copolymer used as a starting material for a film was determined by gel permeation chromatography (GPC) under the following conditions:
- Column: Shodex (registered trademark) HFIP-G (1 column), HFIP-606M (2 columns) (Shodex)
- Solvent: Hexafluoroisopropanol (supplemented with 5 mM sodium trifluoroacetate)
- Flow rate: 0.2 mL/min
- Column temperature: 40° C.
- Sample preparation: A solvent (2 mL) was added to a sample (about 1 mg), and the mixture was gently stirred at room temperature (sample concentration: about 0.05% w/v) and filtered through a 0.45 μm filter.
- Injection amount: 0.020 mL
- Reference sample: Monodisperse polymethyl methacrylate
- Detector: Differential refractive index detector RI (RI-104 type; Showa Denko K. K.; sensitivity: 32).

(2) Mass Percentages and Average Molecular Weights of the Polyalkylene Glycol Block and the Polyhydroxyalkanoic Acid Block The mass percentages and average molecular weights of the polyalkylene glycol block and the polyhydroxyalkanoic acid block constituting the block copolymer were calculated by the method described herein based on the measurement results of the block copolymer.

(3) Self-Support Ability

Self-support ability was evaluated for the films prepared by spin coating using the starting material polymers of Examples 1 to 3 and Comparative Examples 1 to 5. Table 1 shows the results. The expression "self-support ability" of a film refers to a property that allows a film to maintain its shape without a support. More specifically, a polymer film was allowed to float in water to be present in gas-liquid interface for 3 hours. When the rate of decrease in film thickness was 10% or less, the polymer film was evaluated as having self-support ability. When the polymer film was expanded so that the rate of decrease in film thickness was more than 10%, the polymer film was evaluated as having no self-support ability.

The presence of a film in water was not confirmed for the polymer films obtained using the starting material polymers of Comparative Examples 3 and 4. The polymer films obtained using the starting material polymers of Comparative Examples 2 and 5 were confirmed to have an increase in the film surface area and a significant decrease in the film thickness after the elapse of 3 hours, compared with the levels at the time of film formation, indicating poor film stability. Substantially no changes were observed in the film surface area and film thickness for the polymer films obtained using the starting material polymers of Examples 1, 2, and 3 and Comparative Example 1, indicating that the films were stably present in gas-liquid interface even after the elapse of 3 hours.

TABLE 1

| Starting material polymer | Self-support ability |
| --- | --- |
| Example 1 | Observed |
| Example 2 | Observed |
| Example 3 | Observed |
| Comparative Example 1 | Observed |
| Comparative Example 2 | Not observed |
| Comparative Example 3 | Not observed |
| Comparative Example 4 | Not observed |
| Comparative Example 5 | Not observed |

(4) Determination of Film Thickness

Film thickness was measured for the films prepared by gravure coating using the starting material polymers of Examples 1, 2, and 3 and Comparative Example 1. Measurement was conducted by observing an area (100 μm×25 μm) of each polymer film using an atomic force microscope (nano-scale hybrid microscope VN-8000; Keyence Corporation; tapping mode).

(5) Young's Modulus

The Young's modulus was determined for the polymer films prepared by gravure coating using the starting material polymers of Examples 1, 2, and 3 and Comparative Example 1. The Young's modulus was determined in the manner described below by the Strain-Induced Elastic Buckling Instability for Mechanical Measurements (SIEBIMM) technique.

A polydimethylpolysiloxane (PDMS) (Sylgard 184 (registered trademark); Dow Corning Toray Co., Ltd.) having a 3-cm square size was extended on a 3.6-cm square Teflon (registered trademark) substrate in one direction. A polymer film to be measured was attached thereto. Wrinkles were formed on the polymer film by force generated when the shape of the polymer film bonded to the PDMS base material returned to the original shape. Intervals between wrinkles were measured and the Young's modulus was calculated by Formula (3):

$$Es = \frac{3 \times (1 - v_s^2) Ef}{(1/vf^2) \times (\lambda/2\pi h)^3} \quad (3)$$

$E_s$: Young's modulus or the measurement sample
$E_f$: Young's modulus of the PDMS base material (1.8 MPa)
$v_s$: Poisson's ratio of the measurement sample (0.33)
$v_f$: Poisson's ratio of the PDMS base material (0.5)
$\lambda$: Wrinkle wavelength
h: Film thickness of the measurement sample.

Table 2 summarizes the measurement results of the film thickness and Young's modulus. The Young's modulus of the polymer film comprising the polymer of Example 1 containing 25% by mass of a polyethylene glycol block was smaller than that of the polymer film comprising the polymer of Comparative Example 1 containing no polyethylene glycol block. In addition, although the Young's modulus could not be calculated for the polymer films comprising the polymers of Examples 2 and 3, it was observed that wrinkles formed on the polymer film quickly disappeared. It was therefore considered that the Young's modulus for the polymer films was lower than a Young's modulus of 64 MPa for the polymer film comprising the polymer of Example 1 and having a film thickness of 312 nm that was comparable to the film thicknesses of the polymer films. In addition, the polymer films had sufficient handleability. Accordingly, the Young's modulus was assumed to be 20 MPa or more.

TABLE 2

| Starting material polymer | Film thickness (nm) | Young's modulus (MPa) |
| --- | --- | --- |
| Example 1 | 84 | 78 |
| Example 1 | 104 | 52 |
| Example 1 | 312 | 64 |
| Example 2 | 323 | Not calculable |
| Example 3 | 353 | Not calculable |
| Comparative Example 1 | 89 | 710 |
| Comparative Example 1 | 105 | 780 |

(6) Contact Angle

The polymer film was scooped on a silicon substrate and dried overnight at room temperature. Water (4 μl) was added dropwise to the surface of the polymer film surface and the contact angle was observed using a digital microscope (Asahikogaku Manuf. Co. Lt., MS-200) from the side view. The contact angle formed 30 seconds after the dropwise addition of water was defined as a static contact angle, and the contact angle formed when the droplet interface was receding along with water evaporation of water droplets was defined as a receding contact angle. Both contact angles were measured.

Table 3 summarizes the measurement results for the polymer films comprising polymers of Example 1, 2 and 3, and Comparative Example 1 prepared by gravure coating. The static contact angle was almost the same for each polymer film. Meanwhile, the receding contact angles for the polymer films comprising the polymers of Example 1, 2 and 3 each containing a polyethylene glycol block were smaller than the receding contact angle for the polymer film comprising the polymer of Comparative Example 1 containing no polyethylene glycol block. This revealed that wettability was improved.

TABLE 3

| Starting material polymer | Static contact angle (deg) | Receding contact angle (deg) |
|---|---|---|
| Example 1 | 68 | 39 |
| Example 2 | 71 | 34 |
| Example 3 | 72 | 36 |
| Comparative Example 1 | 67 | 60 |

(7) Adherability Test

Each polymer film having a size of 1×1 cm$^2$ was attached to the surface of the "Bio Skin" arm model (skin model No. 47; Beaulax Co., Ltd.). After the elapse of 6 hours, various types of commercially available adhesive tapes were applied thereto. Then, each tape was detached by an angle of about 60°. When the polymer film was not detached, it was judged that strength of adherence of the polymer film to an object was high. When the polymer film was detached together with the adhesive tape, it was judged that the strength of adherence of the polymer film to an object was low. The test results were evaluated as follows. Scores "5," "4," "3," "2," "1," and "0" were given to polymer film detachment rates of 65% or more, 35% to 65%, 15% to 35%, 5% to 15%, 5% or less, and 0%, respectively. Adhesive force of each adhesive tape was specified herein as a value calculated by the 90° peeling test of JIS Z 0237.

Table 4 shows the results of the adherability test for the polymer films obtained using the starting material polymers of Examples 1, 2 and 3 and Comparative Example 1. The polymer films obtained using the polymers of Examples 1, 2 and 3, for which the Young's modulus was 100 MPa or less, showed higher levels of adherability than that for the polymer film obtained using the polymer of Comparative Example 1, for which the Young's modulus was more than 100 MPa.

TABLE 4

| Adhesive force of tape (N/cm) | Example 1 Film thickness: 104 nm | Example 2 Film thickness: 323 nm | Example 3 Film thickness: 353 nm | Comparative Example 1 Film thickness: 105 nm |
|---|---|---|---|---|
| 0.22 | 3 | 1 | 2 | 5 |
| 0.78 | 5 | 5 | 5 | — |
| 1.18 | — | 5 | 5 | — |

(8) Evaluation of Ability to Prevent Adhesion Using the Serosal Dissection Model Mouse Laparotomy was performed on 11- to 12-week old female mice (C57BL6 lineage; body weight: 22 to 25 g; CLEA Japan Inc.) under ether anesthesia. The abdominal wall of the flank was raised with forceps and a cut was made using scissors such that a circle hole (φ 1 mm) was formed on the peritoneal membrane. A laminated film formed by laminating a water-soluble film (pullulan film) and a polymer film was arranged at the wound site. The water-soluble film was dissolved in physiological saline so that the polymer film was attached to the wound site. The dissolution procedure was carried out while removing moisture with waste cloth. As comparative groups, a group for which Seprafilm (registered trademark; Kaken Pharmaceutical Co., Ltd.) purchased as a commercially available antiadhesive film was applied (positive control) and a group for which a covering material was not applied (negative control) were used.

Laparotomy was performed again 1 week after surgery. The degree of adhesion between the wound and other organs was evaluated using the following 5-level adhesion scores (scores 1 to 5). The FIGURE summarizes the evaluation results.

Score 1: No adhesion.
Score 2: Although adhesion is observed, the other organs can be easily detached via gravity or the like.
Score 3: Blunt dissection is necessary.
Score 4: Sharp dissection is necessary.
Score 5: Loss of tissue is observed upon dissection.

All publications, patents, and patent applications cited herein are incorporated by reference in their entirety.

The invention claimed is:

1. A polymer film comprising a block copolymer having a structure in which branched polyalkylene glycol and polyhydroxyalkanoic acid are bound to each other, wherein
   the branched polyalkylene glycol has at least three terminal hydroxyl groups per molecule,
   mass percentage of the branched polyalkylene glycol relative to the total mass of the block copolymer is 1% to 30%,
   a value obtained by dividing average molecular weight of polyhydroxyalkanoic acid in the block copolymer by X that is the number of terminal hydroxyl groups present per a single molecule of the branched polyalkylene glycol is 10000 to 30000, and
   the polymer film is two dimensional and has a film thickness of 80 to 400 nm.

2. The polymer film according to claim 1, wherein the branched polyalkylene glycol has a structure in which linear polyethylene glycol is bound to polyalcohol.

3. The polymer film according to claim 1, wherein the branched polyalkylene glycol has 3 to 8 terminal hydroxyl groups.

4. The polymer film according to claim 1, wherein the branched polyalkylene glycol has an average molecular weight of 5000 to 30000.

5. The polymer film according to claim 1, wherein the block copolymer has an average molecular weight of 40000 to 200000.

6. The polymer film according to claim 1, wherein the block copolymer is represented by formula (I):

where m denotes an integer of 0 to 4, each of n, o, p, q, and r independently denotes an integer of 36 to 126, each of v, w, x, y, and z independently denotes an integer of 91 to 376 or formula (II):

(II)

where s denotes an integer of 81 to 126, and t denotes an integer of 220 to 377.

7. The polymer film according to claim 1, wherein the Young's modulus is 20 MPa to 700 MPa.

8. The polymer film according to claim 1, having a receding contact angle less than 60°.

9. A laminated film, wherein a water-soluble film comprising a water-soluble polymer is laminated on at least one side of the polymer film according to claim 1.

10. An antiadhesive material comprising a laminated film according to claim 9.

11. An antiadhesive material comprising the polymer film according to claim 1.

* * * * *